(12) United States Patent
Kauffmann

(10) Patent No.: US 10,850,280 B2
(45) Date of Patent: Dec. 1, 2020

(54) METHOD FOR INTERNALLY COATING A LIQUID TEST SAMPLE COLLECTION DEVICE WITH AT LEAST ONE ANTICOAGULANT COMPOUND, AND DEVICES AND KITS RELATED THERETO

(71) Applicant: Siemens Healthcare Diagnostics Inc., Tarrytown, NY (US)

(72) Inventor: Aaron Kauffmann, Elkhart, IN (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 81 days.

(21) Appl. No.: 16/190,672

(22) Filed: Nov. 14, 2018

(65) Prior Publication Data
US 2019/0151851 A1    May 23, 2019

Related U.S. Application Data

(60) Provisional application No. 62/587,648, filed on Nov. 17, 2017.

(51) Int. Cl.
*B01L 3/00*    (2006.01)
*A61L 33/00*    (2006.01)

(52) U.S. Cl.
CPC .......... *B01L 3/52* (2013.01); *A61L 33/0011* (2013.01); *A61L 33/0041* (2013.01); *B01L 3/527* (2013.01); *A61L 2420/02* (2013.01); *B01L 2200/12* (2013.01); *B01L 2200/16* (2013.01); *B01L 2300/16* (2013.01)

(58) Field of Classification Search
CPC ...... B01L 3/52; B01L 33/527; B01L 2200/12; B01L 2200/16; B01L 2300/16; A61L 33/0011; A61L 33/0041; A61L 2420/02
See application file for complete search history.

(56) References Cited

U.S. PATENT DOCUMENTS 6,121,055 A * 9/2000 Hargreaves ............. B01L 3/502
435/2

* cited by examiner

*Primary Examiner* — Gailene Gabel
(74) *Attorney, Agent, or Firm* — Dunlap Codding P.C.

(57) ABSTRACT

Methods, devices, and kits, related to embodiments for uniformly coating at least one inner surface of a capillary with at least one anticoagulant compound.

8 Claims, 12 Drawing Sheets

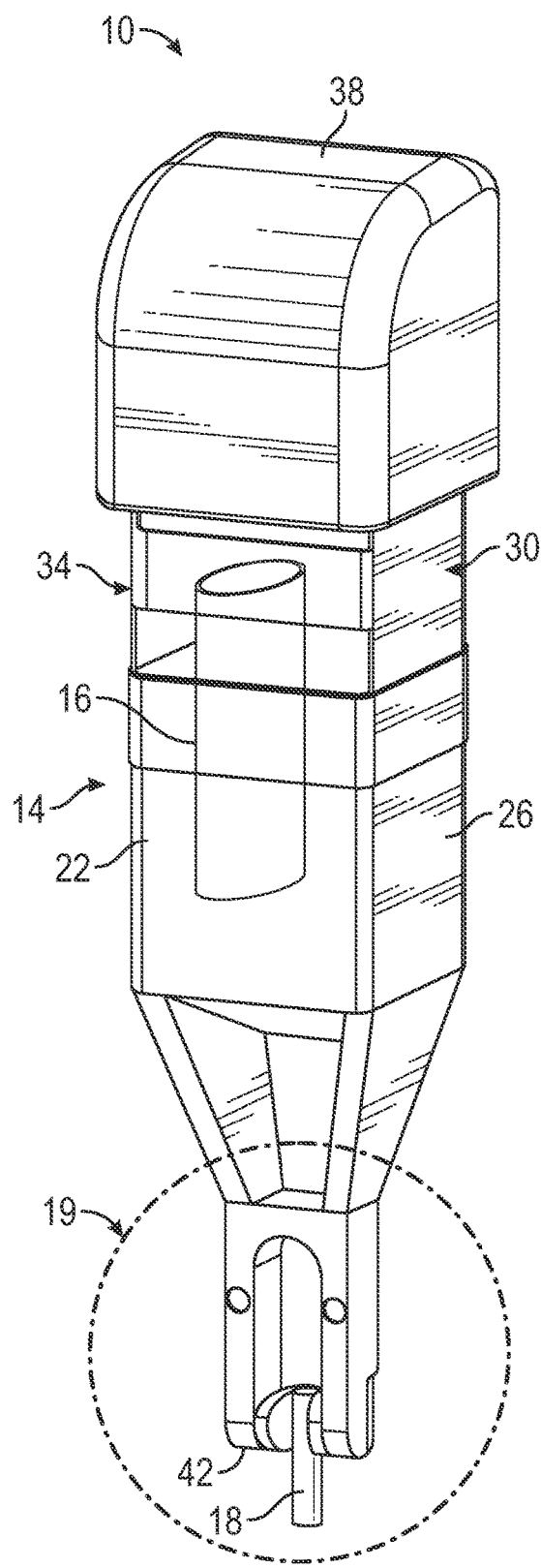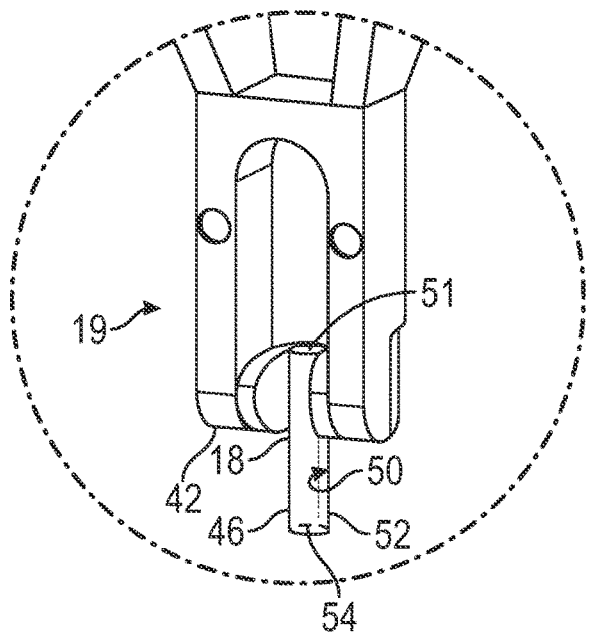
FIG. 1
FIG. 2

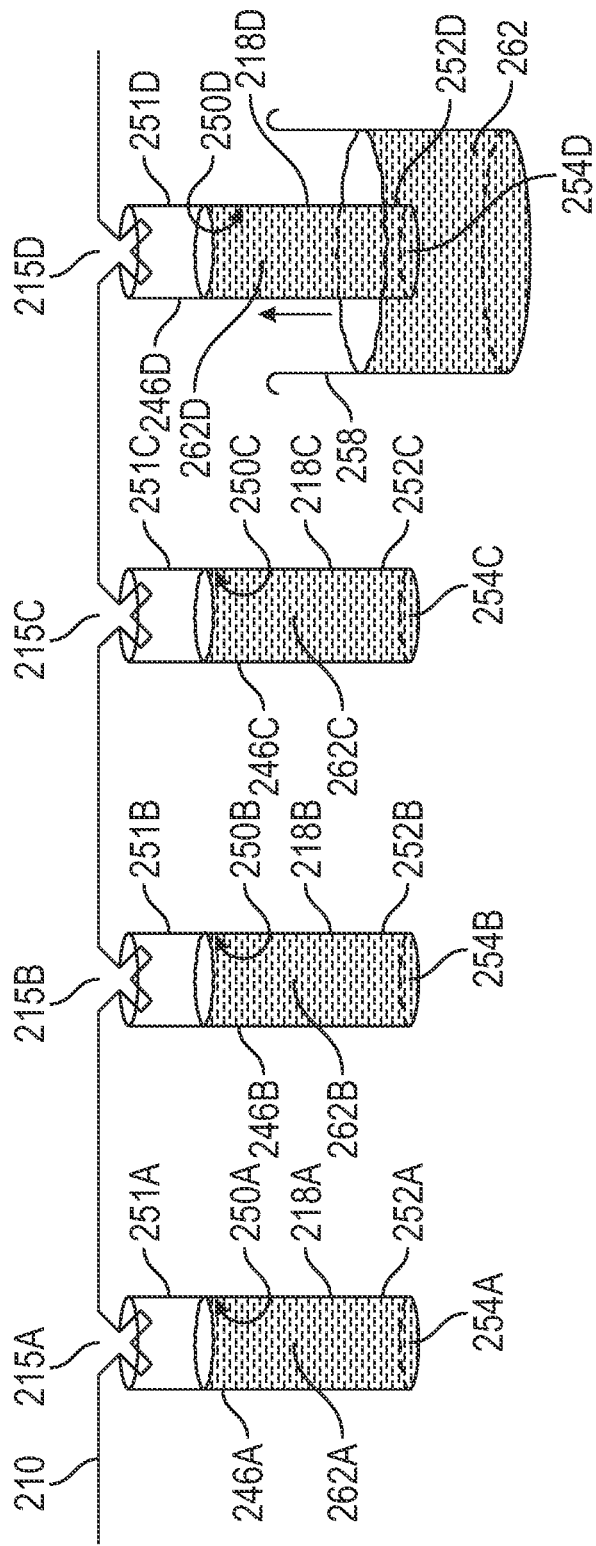

METHOD FOR INTERNALLY COATING A LIQUID TEST SAMPLE COLLECTION DEVICE WITH AT LEAST ONE ANTICOAGULANT COMPOUND, AND DEVICES AND KITS RELATED THERETO

CROSS REFERENCE TO RELATED APPLICATIONS

This application claims the benefit of U.S. Provisional Application No. 62/587,648, filed Nov. 17, 2017, the contents of which are fully incorporated in their entirety herein by reference.

STATEMENT REGARDING FEDERALLY FUNDED RESEARCH OR DEVELOPMENT

Not Applicable.

TECHNICAL FIELD

The presently disclosed and claimed inventive concept(s) relate to a method(s), device(s), and kit(s) for uniformly depositing and/or coating at least one internal surface of a liquid test sample dispensing device with at least one compound. More specifically, the presently disclosed and claimed inventive concept(s) relate to an improved method that comprises uniformly depositing and/or coating heparin on at least one inner surface of a capillary of a liquid test sample dispensing device for the conductance of at least one analyte(s) detection/diagnostic assay, as well as device(s) and kit(s) related thereto.

BACKGROUND

Numerous devices, kits, and methods exist for injecting liquid test samples within a reaction vessel for conducting diagnostic assays that detect analytes that may be present in the liquid test samples. Such devices have been proven to be effective in diagnostic assays that detect the presence and quantity of certain analytes indicative of a patient's health, including, but not limited to, glycated hemoglobin (HbA1c), microalbumin and creatinine, and lipid-based analytes, such as cholesterol, triglycerides, and/or high-density lipoproteins. However, when conducting diagnostic assays on a patient's liquid test sample, it is important that the liquid test sample dispensing device remains unobstructed in order to both: (i) fully receive the patient's liquid test sample within the device (for instance, via a capillary of the device); and (ii) fully dispense the patient's liquid test sample into, by way of example, a reaction vessel for the conductance of at least one diagnostic assay(s).

In an effort to keep a patient's liquid test sample (e.g., blood) from thickening or coagulating within the capillary of the liquid test sample dispensing device, a portion of the capillary (for instance, at least one inner surface of the capillary) may be coated and/or impregnated with an anticoagulant compound(s), such as, by way of example only, heparin. However, current coating methodologies often result in the creation of at least one crystalline or solid granular heparin plug within the capillary of the liquid test sample dispensing device. Such crystalline or solid granular heparin plugs greatly inhibit (or even destroy) the ability of the liquid test sample dispensing device (i.e., the capillary of the device) to both draw-in the patient's blood sample and to effectively and fully dispense the patient's liquid test sample into a reaction vessel for the conductance of one or more diagnostic assays.

Accordingly, there is a need for improved methodologies that uniformly disperses an anticoagulant compound (such as, by way of example, heparin) on at least one inner surface of liquid test sample dispensing device (such as, by way of example, at least one inner surface of a capillary of the liquid test sample dispensing device). Such improved methodologies, devices, and kits thereby allow, by way of example, and not by way of limitation, for: (1) the uniform coating of the at least one inner surface of the capillary of the liquid test sample dispensing device; (2) a mitigation, if not elimination, of the formation of crystalline or solid granular heparin plugs that obstruct (or destroy) both the intake and outflow of the patient's liquid test sample into and from the capillary of the liquid test sample dispensing device; and (3) an increase in the hold time of a patient's liquid test sample within the capillary of the liquid test sample dispensing device (i.e., the amount of time a patient's blood sample may be within the capillary before it begins to thicken or coagulate). It is to such method(s), device(s), and kit(s), that the presently disclosed and claimed inventive concept(s) is directed.

DESCRIPTION OF THE SEVERAL VIEWS OF THE DRAWINGS

FIG. 1 is a perspective view of one non-limiting embodiment of an improved liquid test sample dispensing device constructed in accordance with the presently disclosed and/or claimed inventive concept(s).

FIG. 2 is an enlarged, perspective view of the capillary portion of the improved liquid test sample dispensing device of FIG. 1.

FIGS. 5A-5H are perspective views of an alternative embodiment of a method for applying at least one anticoagulant compound on at least one inner surface of a plurality of capillaries in accordance with the presently disclosed and/or claimed inventive concept(s), wherein FIGS. 5A-5B illustrate applying at least one anticoagulant compound to a first capillary, FIGS. 5C-5D illustrate applying the at least one anticoagulant compound to a second capillary, FIGS. 5E-5F illustrate applying the at least one anticoagulant compound to a third capillary, and FIGS. 5G-5H illustrate applying the at least one anticoagulant compound to a fourth capillary.

DETAILED DESCRIPTION

Figure 3A:
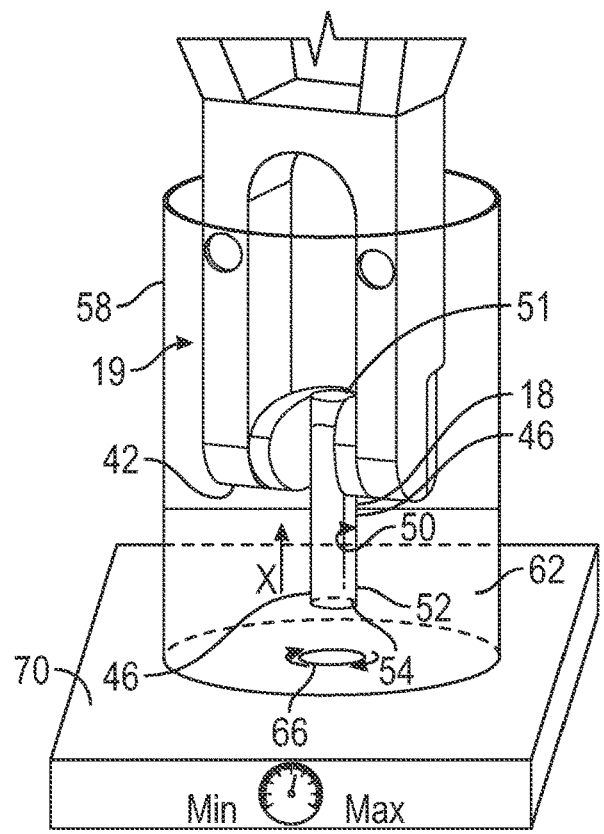
FIG. 3A is a perspective view of the capillary portion of FIG. 2 in which at least one inner surface of the capillary is in fluid contact with a colloidal solution comprising at least one anticoagulant compound and at least one insoluble volatile compound.

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "anticoagulant compound(s)" as used herein will be understood to be any polarized chemical substance or combination of polarized chemical substances that prevents or reduces the coagulation of a patient's blood sample, thereby prolonging the clotting time of the patient's blood sample. Such anticoagulant compound(s) include, but are not limited to, 4-hydroxycoumarin compounds, such as, by way of example only, acenocoumarol, dicoumarol, ethyl bicoumacetate, atromentin, phenindione, phenprocoumon, tecafarin, and warfarin, as well as such other compounds, including, but not limited to, coumarin, heparin and heparin derivatives, fondaparinux, idraparinux, direct factor Xa inhibitors, such as, by way of example only, rivaroxaban, apixaban, edoxaban, betrixaban, darexaban, letaxaban, and eribaxaban, direct thrombin inhibitors, including, without limitation, hirudin, lepirudin, bivalirudin, argatroban, and dabigatran, as well as other types of anticoagulants, including, but not limited to, batraxobin, hementin, vitamin E, ethylenediaminetetraacetic acid (EDTA), citrate, oxalate, and any combinations of any of the above. In one non-limiting embodiment, the anticoagulant compound(s) is heparin.

The term "insoluble volatile compound(s)" as used herein will be understood to be any non-polar (or weakly-polar) solvent(s) whose boiling point is lower than the melting point of a particular anticoagulant compound(s). Non-limiting examples of insoluble volatile compound(s) utilized in accordance with the presently disclosed and/or claimed inventive concept(s) include, but are not limited to, acetone, benzene, ethyl acetate, hexane, methyl acetate, toluene, and combinations thereof. In one non-limiting embodiment, the insoluble volatile compound(s) is acetone.

The term "liquid test sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. In one non-limiting embodiment of the presently disclosed and/or claimed inventive concept(s), the liquid test sample is whole blood. As used herein, the term "volume" as it relates to the liquid test sample utilized in accordance with the presently disclosed and claimed inventive concept(s) means from about 0.1 microliter to about 100 microliters, or from about 1 microliter to about 75 microliters, or from about 2 microliters to about 60 microliters, or less than or equal to about 50 microliters, or less than or equal to about 40 microliters. In one non-limiting embodiment of the presently disclosed and/or claimed inventive concept(s), the liquid test sample is about 1 microliter of whole blood.

The terms "capillary action" and/or "capillary force" as used herein will be understood to include the interaction between contacting surfaces of a liquid and a solid that distorts the liquid surface from a planar shape and causes the liquid rise, fall, or remain contained in a narrow tube, channel, and/or cavity. By way of example only, and not by way of limitation, capillary action includes: (1) the wicking of the colloidal solution comprising at least one anticoagulant compound (such as, by way of example only, heparin) and at least one insoluble volatile compound (such as, by way of example only, acetone) into the capillary of the liquid test sample dispensing device; and (2) the wicking of the liquid test sample into the capillary of the liquid test sample dispensing device, such that the liquid test sample remains in the capillary until agitated.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

The term "reaction vessel" includes any device(s) capable of performing at least one diagnostic assay as described herein. The reaction vessel may perform the diagnostic assay(s) manually, but, in most instances, the reaction vessel will be inserted into a system that automates the performance of the diagnostic assay(s). In one non-limiting embodiment, the reaction vessel comprises a reaction cassette for use in automated diagnostic assays conducted by the DCA Vantage® Analyzer commercially available from Siemens Healthcare Diagnostics, Inc.

Turning now to particular embodiments, the presently disclosed and claimed inventive concept(s) relate to a method(s), device(s), and kit(s) for uniformly coating at least one inner surface of a capillary of a liquid test sample dispensing device with at least one anticoagulant compound(s). More specifically, the presently disclosed and claimed inventive concept(s) relate to an improved methodology for uniformly coating at least one inner surface of a capillary of a liquid test sample dispensing device with heparin, and devices and kits related thereto. The presently disclosed and claimed inventive concept(s) inhibit and/or eliminate the formation of crystalline or solid granular heparin plugs that form within the capillary which impede or destroy the in-flow and out-flow of the capillary.

It is contemplated that virtually any reagent used in the fields of biological, chemical, or biochemical analyses and assays could be used in the devices, kits, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Any method of detecting and measuring the analyte in a fluid sample can be used in the devices, kits, and methods of the presently claimed and inventive concepts. A variety of assays for detecting analytes are well known in the art and include, but are not limited to, chemical assays, enzyme inhibition assays, antibody stains, latex agglutination, latex agglutination inhibition and immunoassays, such as, radioimmunoassays. The term "antibody" herein is used in the broadest sense and refers to, for example, intact monoclonal antibodies, polyclonal antibodies, multi-specific antibodies (e.g., bispecific antibodies), and to antibody fragments that exhibit the desired biological activity (e.g., antigen/analyte-binding). The antibody can be of any type or class (e.g., IgG, IgE, IgM, IgD, and IgA) or sub-class (e.g., IgG1, IgG2, IgG3, IgG4, IgA1, and IgA2).

While immunoassays (including, but not limited to, sequential analytical chemical and immunoassays) are primarily discussed herein for the detection of at least one analyte of interest present in a liquid test sample, a person having ordinary skill in the art should readily understand that the presently disclosed and claimed inventive concept(s) are not strictly limited to immunoassays and may include, by way of example and not by limitation, chemical and chemical-based assays, nucleic acid assays, lipid-based assays, and serology-based assays. Immunoassays, including radioimmunoassays and enzyme-linked immunoassays, are useful methods for use with the presently claimed and disclosed inventive concepts. A variety of immunoassay formats, including, for example, competitive and non-competitive immunoassay formats, antigen/analyte capture assays and two-antibody sandwich assays can be used in the methods of the invention. Enzyme-linked immunosorbent assays (ELISAs) can be used in the presently claimed and disclosed inventive concepts, as well. In the case of an enzyme immunoassay, an enzyme is typically conjugated to a second antibody, generally by means of glutaraldehyde, periodate, hetero-bifunctional crosslinking agents, or biotin-streptavidin complexes. As will be readily recognized, however, a wide variety of different conjugation techniques exist which are readily available for use with the presently disclosed and claimed inventive concept(s) to one skilled in the art.

Assays, including, but not limited to, immunoassays, nucleic acid capture assays, lipid-based assays, and serology-based assays, can be developed for a multiplexed panel of proteins, peptides, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin, myoglobin, α-1-microglobin, immunoglobins, enzymes, proteins, glycoproteins, protease inhibitors, drugs, cytokines, creatinine, and glucose. The device(s), kit(s), and method(s) disclosed and/or claimed herein may be used for the analysis of any liquid test sample, including, without limitation, whole blood, plasma, serum, or urine.

Referring now to the Figures, and more particularly to FIG. 1, shown therein is a non-limiting embodiment of a liquid test sample dispensing device 10 that both collects a patient's liquid test sample and dispenses a patient's liquid test sample into a reaction vessel for the conductance of at least one diagnostic assay. In one non-limiting embodiment of the presently disclosed and/or claimed inventive concept(s), the liquid test sample dispensing device 10 comprises a body 14, a liquid waste collector 16, and a capillary 18. While shown in FIGS. 1 and 4 as comprising the liquid waste collector 16, a person having ordinary skill in the art should readily appreciate that the liquid test sample dispensing device 10 is fully functional and fully satisfies any and all objectives of the presently disclosed and/or claimed inventive concept(s) with or without the inclusion of the liquid waste collector 16.

In one non-limiting embodiment, and as shown in FIG. 1, the body 14 comprises a first side 22, a second side 26, a third side 30, a fourth side 34, a first end 38, and a second end 42. While depicted in FIG. 1 as comprising four sides, it should be readily understood that the body 14 can comprise any number of sides that accomplishes the presently disclosed and/or claimed inventive concept(s), including, without limitation, the body 14 may comprise 1, 2, 3, 4, 5, 6, 7, 8, 9, 10, 11, 12, 13, 14, 15, 16, 17, 18, 19, 20, 30, 40, 50, 60, 70, 80, 90, or greater than or equal to 100 sides. In addition, while shown in FIG. 1 as being substantially rectangular in shape, the body 14 can be configured to be any shape that accomplishes the presently disclosed and/or claimed inventive concept(s), including, without limitation, cylindrical, ovular, triangular prism, cube, rectangular prism, trapezoidal prism, pentagonal prism, hexagonal prism, heptagonal prism, octagonal prism, nonagonal prism, decagonal prism, or any polygonal prism (in which case, the number of sides will comport with the particular shape of the body 14—i.e., an octagonal prism-shaped body 14 comprises eight sides/faces). As shown in greater detail in FIG. 4, the body 14 of the liquid test sample dispensing device 10 is configured so as to be received in a reaction vessel wherein a patient's liquid test sample is dispensed from the capillary 18 into the reaction vessel for the conductance of at least one diagnostic assay, such as, by way of example only, a glycated hemoglobin diagnostic assay.

In certain non-limiting embodiments, the body 14 (and/or the capillary 18) is fabricated as a molded, unitary component formed of a rigid plastic material (so as to avoid deformation of the body 14 when both collecting a patient's liquid test sample and/or inserting the body into a reaction vessel), including, for example, synthetic and/or naturally-occurring or derived polymers (both organic and/or inorganic), such as, by way of example only, thermoplastic polymer(s), thermoset polymer(s), elastomer(s), and/or synthetic fiber(s) such as low-density polyethylene, high-density polyethylene, polystyrene, polyvinylchloride, styrene butadiene, acrylic(s), polyacrylics, and polyvinyl acetate, and/or soda-lime, and combinations thereof. However, a person having ordinary skill in the art should readily appreciate that the body 14 may be constructed of any material capable of accomplishing the presently disclosed and/or claimed inventive concept(s). In one non-limiting embodiment (as shown in FIG. 1), the body 14 of the liquid test sample dispensing device 10 is constructed such that the area defined by the first side 22, second side 26, third side 30, and fourth side 34 of the body 14 is hollow, in which the liquid waste collector 16, then present, resides. In one non-limiting embodiment, the first side 22 and the third side 30 are open such that the liquid waste produced as a by-product during the conductance of at least one diagnostic assay is brought into contact with, when present, the liquid waste collector 16 for the removal and containment of the liquid waste; however, a person having ordinary skill in the art should readily understand that any or all of the sides of the body 14 may be open to allow for the interface between the liquid waste and the liquid waste collector 16.

In another non-limiting embodiment, the area defined by the first side 22, second side 26, third side 30, and fourth side 34 of the body 14 need not be hollow (or include the liquid waste collector 16). For instance, by way of example only, the area defined by the first side 22, second side 26, third side 30, and fourth side 34 of the body 14 may be solid, with no hollow spaces defined therein. In addition, rather than comprising the liquid waste collector 16, an optional plurality of micro-cavities (not shown) may be disposed on and formed in one or all of the first side 22, second side 26, third side 30, and fourth side 34 of the body 14 for the collection of liquid waste produced as a by-product of conducting at least one diagnostic assay.

When present within the liquid test sample dispensing device 10, the liquid waste collector 16 is adapted to and formed of a material(s) that collects the liquid waste produced as a by-product of conducting at least one diagnostic assay. While shown in FIG. 1 as being substantially cylindrical in shape, a person having ordinary skill in the art should understand that, when present, the liquid waste collector 16 can be any shape capable of accomplishing the presently disclosed and/or claimed inventive concept(s), including, without limitation, triangular prism, cube, rectangular prism, trapezoidal prism, pentagonal prism, hexagonal prism, heptagonal prism, octagonal prism, nonagonal prism, decagonal prism, or any polygonal prism (in which case, the number of sides will comport with the particular shape of the liquid waste collector 16—i.e., an octagonal prism-shaped liquid waste collector 16 comprises eight sides/faces). The liquid waste collector 16 can be constructed of any material or combination of materials that accomplishes the presently disclosed and/or claimed inventive concept(s), namely the absorbance and containment of liquid waste (which comprises a combination of used and unused diagnostic assay reaction reagents and the patient's liquid test sample). Such materials include, but are not limited to, cellulosic or fiber-based products, including, without limitation, paper, cotton, sponge, and cellulose acetate, as well as polymeric materials, including superabsorbent polymers, and any combinations of any of the above.

The capillary 18 is adapted to collect a patient's liquid test sample and to subsequently inject the liquid test sample into a reaction vessel. In addition, as shown in greater detail in FIG. 3A, the capillary 18 is adapted to collect a colloidal solution comprising at least one anticoagulant compound (such as, by way of example only, heparin) and at least insoluble volatile compound (such as, by way of example only, acetone). In one non-limiting embodiment, the capillary 18 collects the colloidal solution and the patient's liquid fluid sample via capillary action when the capillary 18 is in contact with the colloidal solution and/or the patient's liquid test sample, respectively. However, a person having ordinary skill in the art should readily appreciate that the colloidal solution and/or the patient's liquid test sample can be collected by the capillary 18 via any method commonly known in the art, including, without limitation, via creation of a negative pressure differential that draws either the colloidal solution and/or the patient's liquid test sample into the capillary 18. The capillary 18 can be constructed of any material(s) commonly known in the art, including, without limitation, glass and/or chemically-inert plastic(s). The size and volume-capacity of the capillary 18 will vary depending on: (1) the volume of colloidal solution necessary to uniformly coat at least one inner surface of the capillary 18; and (2) the type and quantity of the patient's liquid test sample being collected. In certain non-limiting embodiments, the capillary 18 may be adapted and sized to hold volumes of from about 0.1 microliter to about 100 microliters, or from about 0.5 microliters to about 95 microliters, or from about 1 microliter to about 90 microliters, or from about 2 microliters to about 85 microliters, or from about 5 microliters to about 80 microliters, or from about 10 microliters to about 75 microliters, or from about 15 microliters to about 70 microliters, or from about 20 microliters to about 65 microliters, or from about 25 microliters to about 60 microliters, or from about 30 microliters to about 55 microliters, or from about 35 to about 50 microliters, or less than or equal to about 40 microliters. By way of example only, and not by way of limitation, the volume capacity of the capillary 18 is about 1 microliter when the patient's liquid test sample is whole blood. In one non-limiting embodiment, and as shown in greater detail in FIGS. 2 and 3A-3D, a first end 51 of the capillary 18 extends through the second end 42 of the body 14 wherein at least a portion of the capillary 18 remains external to the body 14 for collection of the colloidal solution and/or the patient's liquid test sample.

In addition, while depicted in FIG. 1 as being substantially cylindrical in shape, it should be readily understood to a person having ordinary skill in the art that the capillary 18 may be any shape capable of accomplishing the presently disclosed and/or claimed inventive concept(s), including, without limitation, triangular prism, cube, rectangular prism, trapezoidal prism, pentagonal prism, hexagonal prism, heptagonal prism, octagonal prism, nonagonal prism, decagonal prism, or any polygonal prism (in which case, the number of sides will comport with the particular shape of the capillary 18—i.e., an octagonal prism-shaped capillary 18 comprises eight sides/faces). In one non-limiting embodiment, the capillary 18 is substantially cylindrical in shape. In addition, the capillary 18 is adapted to receive liquid materials via capillary action.

Referring now to FIG. 2, shown therein is an enlarged, perspective view of the capillary portion 19 of the improved liquid test sample dispensing device 10 of FIG. 1. As shown in FIG. 2, the capillary portion 19 comprises the capillary 18, the capillary 18 further comprising at least one outer surface 46, at least one inner surface 50, a first end 51, a second end 52, and an opening 54 located at the second end 52 for receiving and dispensing a patient's liquid test sample and/or the colloidal solution via, by way of example only, capillary action.

Referring now to FIG. 3A, shown therein is a perspective view of the capillary portion 19 of FIG. 2 in which the at least one inner surface 50 of the capillary 18 is in fluid contact with a colloidal solution 62 comprising at least one anticoagulant compound(s) and at least one insoluble volatile compound(s). As previously discussed with respect to FIG. 2, the capillary portion 19 comprises the capillary 18, the capillary 18 further comprising at least one outer surface 46, at least one inner surface 50, a first end 51, a second end 52, and an opening 54 at the second end 52.

In one non-limiting embodiment of the presently disclosed and/or claimed inventive concept(s), the at least one anticoagulant compound present in the colloidal solution 62 is heparin. While the concentration of the heparin can vary greatly within the colloidal solution 62, in one non-limiting embodiment, the concentration of the heparin within the colloidal solution 62 ranges from about 0.12 units per milliliters of colloidal solution 62 (or about 0.00024 milligrams per milliliter of colloidal solution 62) to the saturation point of heparin within the volume of the colloidal solution. The term "unit" as used in this paragraph will be understood to mean a Howell unit which is defined as the quantity of heparin required to keep one (1) milliliter of cat's blood fluid for 24 hours at 0° C. and is equivalent to about 0.002 milligrams of heparin.

In one non-limiting embodiment of the presently disclosed and/or claimed inventive concept(s), the capillary portion 19 is placed within a receptacle 58 containing the colloidal solution 62 comprising at least one anticoagulant compound and at least one insoluble volatile compound. In one non-limiting embodiment, the at least one anticoagulant compound is heparin and the at least one insoluble volatile compound is acetone. In order to ensure that the anticoagulant(s) and the insoluble volatile compound(s) remain equally dispersed throughout the colloidal solution 62, an inert stirring device, such as, by way of example only, an inert, magnetic stir bar 66 can be used in conjunction with a magnetic stirrer 70 for the continuous mixing of the colloidal solution 62 within the receptacle 58. Examples of commercially available magnetic stirrers are commonly known in the art. In addition, while shown in FIG. 3A as comprising a receptacle 58, a magnetic stir bar 66, and a magnetic stirrer 70, it should be readily understood to a person having ordinary skill in the art that the colloidal solution 62 may be mixed via any method commonly known in the art, including, by way of example only, via commercial-grade mixers that allow for the mixing of larger batches of the colloidal solution 62 in order to, as shown in greater detail in FIGS. 5A-5H, coat the internal surfaces of multiple capillaries simultaneously either via continuous or batch-processing methods. While shown in FIG. 3A as a single capillary 18, it should be readily understood to a person having ordinary skill in the art that the process of coating at least one inner surface 50 of a capillary 18 can be accomplished in a batch or continuous automated manufacturing process in which the inner surfaces of capillaries of multiple liquid test sample dispensing devices are simultaneously coated with the colloidal solution 62.

As shown in FIG. 3A, in one non-limiting embodiment, the capillary portion 19 is placed within the receptacle 58 such that the opening 54 of the capillary 18 is submerged within the colloidal solution 62. As a result of this submersion, the colloidal solution 62 wicks into the capillary 18 via capillary action (as shown by upward arrow x) through the opening 54 such that the colloidal solution 62 is in fluid communication with at least one portion of the inner surface 50 of the capillary 18. The colloidal solution 62 is maintained in the receptacle 58 at a temperature that is below the evaporation temperature of the at least one insoluble volatile compound of the colloidal solution 62. In one non-limiting embodiment, the at least one insoluble volatile compound is acetone and the temperature of the colloidal solution 62 is maintained in the receptacle 58 in a range from about 0° C. to about 55° C., or from about 5° C. to about 50° C., or from about 10° C. to about 45° C., or from about 15° C. to about 40° C., or from about 20° C. to about 35° C., or from about 25° C. to about 30° C. In one non-limiting embodiment, the colloidal solution 62 is maintained at a temperature of about 25° C.

Figure 3B:
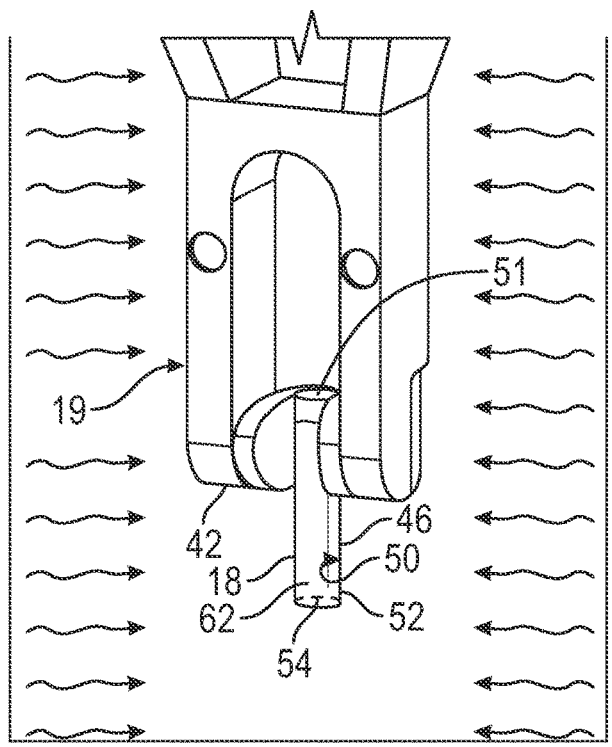
FIG. 3B is a perspective view of the capillary portion of FIG. 3A in which the liquid test sample dispensing device has been placed in a commercial-grade dryer to evaporate the at least one insoluble volatile compound.
Figure 3C:
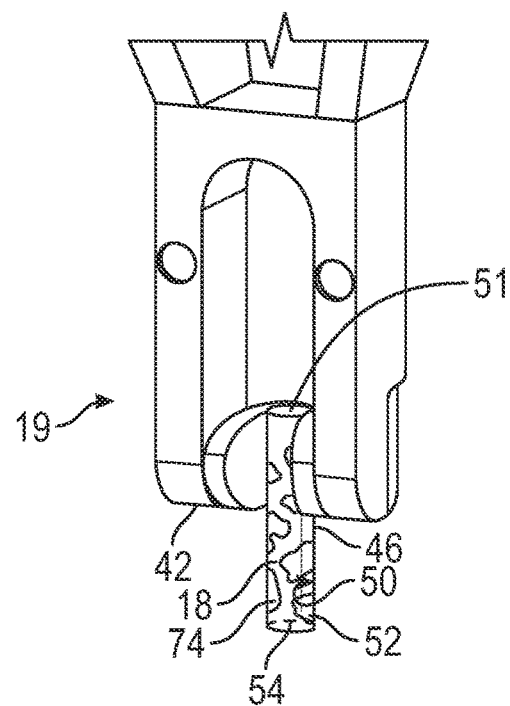
FIG. 3C is a perspective view of the capillary portion of FIG. 3B in which the at least one insoluble volatile compound has been evaporated leaving non-uniform granules of the at least one anticoagulant compound deposited on the at least one inner surface of the capillary.

Referring now to FIG. 3B, once the colloidal solution 62 has been wicked into the capillary 18 via capillary action and is contained therein, the capillary portion 19 (or the entirety of the liquid test sample dispensing device 10) is heated to evaporate off and remove the at least one insoluble volatile compound contained within the colloidal solution 62. The heating at this stage is conducted at a temperature that is high enough to evaporate the insoluble volatile compound(s) (for instance, acetone), but low enough so as not to melt the anticoagulant compound(s) (for instance, heparin granules, which, as shown in greater detail in FIG. 3C, are deposited on the at least one inner surface 50 of the capillary 18 as the insoluble volatile compound(s) evaporates). In one non-limiting embodiment, the at least one insoluble volatile compound is acetone and the colloidal solution 62 contained within the capillary 18 is heated to and maintained at a temperature from about 55° C. to about 125° C., or from about 60° C. to about 120° C., or from about 65° C. to about 115° C., or from about 70° C. to about 110° C., or from about 75° C. to about 105° C., or from about 80° C. to about 100° C., or from about 85° C. to about 95° C., or from about greater than or equal to 90° C. In one non-limiting embodiment, the capillary portion 19 is heated to a temperature of about 100° C. to evaporate off and remove the at least one insoluble volatile compound from the colloidal solution 62 contained within the capillary 18. The capillary portion 19 can be heated via any method commonly known in the art provided that the colloidal solution 62 remains in contact with the at least one inner surface 50 of the capillary 18 prior to and during the evaporation of the at least one insoluble volatile compound(s), including, without limitation, via commercial-grade dryers and/or vacuum dryers commonly known in the art.

Figure 3D:
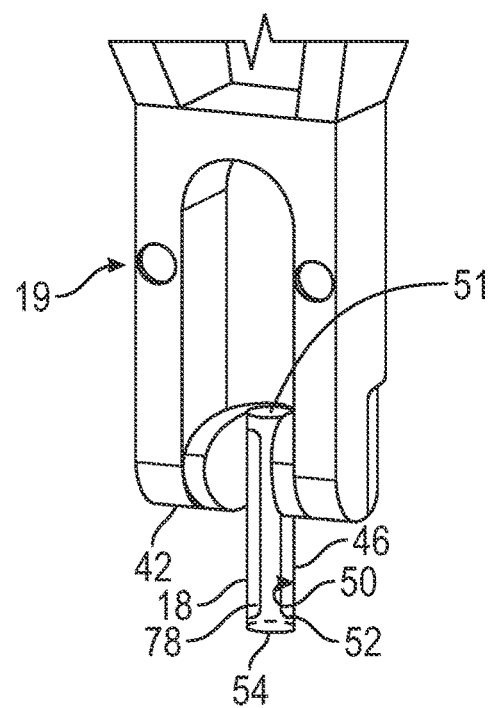
FIG. 3D is a perspective view of the capillary portion of FIG. 3C in which the non-uniform granules of the at least one anticoagulant compound are heated to form a uniform coating of the at least one anticoagulant compound on the at least one inner surface of the capillary.

Referring now to FIG. 3C, shown therein is a perspective view of the capillary portion 19 of FIG. 3B in which the at least one insoluble volatile compound has been evaporated leaving non-uniform anticoagulant compound granules 74 (for instance, heparin granules) deposited on the at least one inner surface 50 of the capillary 18. As can be seen in FIG. 3C, the anticoagulant compound granules 74, due to their potential to form non-uniform shape(s), may form granular plugs within the capillary 18 that inhibit or eliminate the ability of the capillary 18 to effectively draw in a patient's liquid test sample. If present and as shown in FIG. 3D, the non-uniform anticoagulant compound granules 74 may be heated such that the anticoagulant compound granules are melted to form a uniform, even coat 78 which substantially covers the entirety of the at least one inner surface 50 of the capillary 18 without restricting the opening 54 or the bore (not numbered) of the capillary 18 from being able to wick in a patient's liquid test sample via capillary action. When the anticoagulant compound granules 74 are heparin granules, the capillary portion 19 may be heated to a temperature of from about 130° C. to about 200° C., or from about 135° C. to about 195° C., or from about 140° C. to about 190° C., or from about 145° C. to about 185° C., or from about 150° C. to about 180° C., or from about 155° C. to about 175° C., or from about 160° C. to about 170° C., or greater than or equal to about 165° C. to allow the heparin granules to sufficiently melt to form a uniform heparin coating 78 on the at least one inner surface 50 of the capillary 18. The capillary portion 19 may be heated via any method commonly known in the art, including, without limitation, via commercial-grade dryers.

Following either the deposition of anticoagulant granules 74 or, if such anticoagulant granules 74 inhibit and/or restrict the inflow or outflow of the capillary 18, the uniform anticoagulant compound coating 78 of the at least one inner surface 50 of the capillary 18, the capillary 18 is ready to be used to collect (and dispense) a patient's liquid test sample, for instance, a patient's blood sample for the conductance of at least one diagnostic assay. As a result of the uniform anticoagulant compound coating 78, the advantages of the presently disclosed and/or claimed inventive concept(s) are realized, including, but not limited to, (1) mitigating and/or eliminating the clogging of the capillary 18 with non-uniform anticoagulant compound granules 74; and (2) an increase in the amount of time that a patient's liquid test sample (i.e., a patient's blood sample) can be maintained within the capillary 18 prior to being dispensed, for instance, into a reaction vessel, for the conductance of at least one diagnostic assay.

Figure 4:
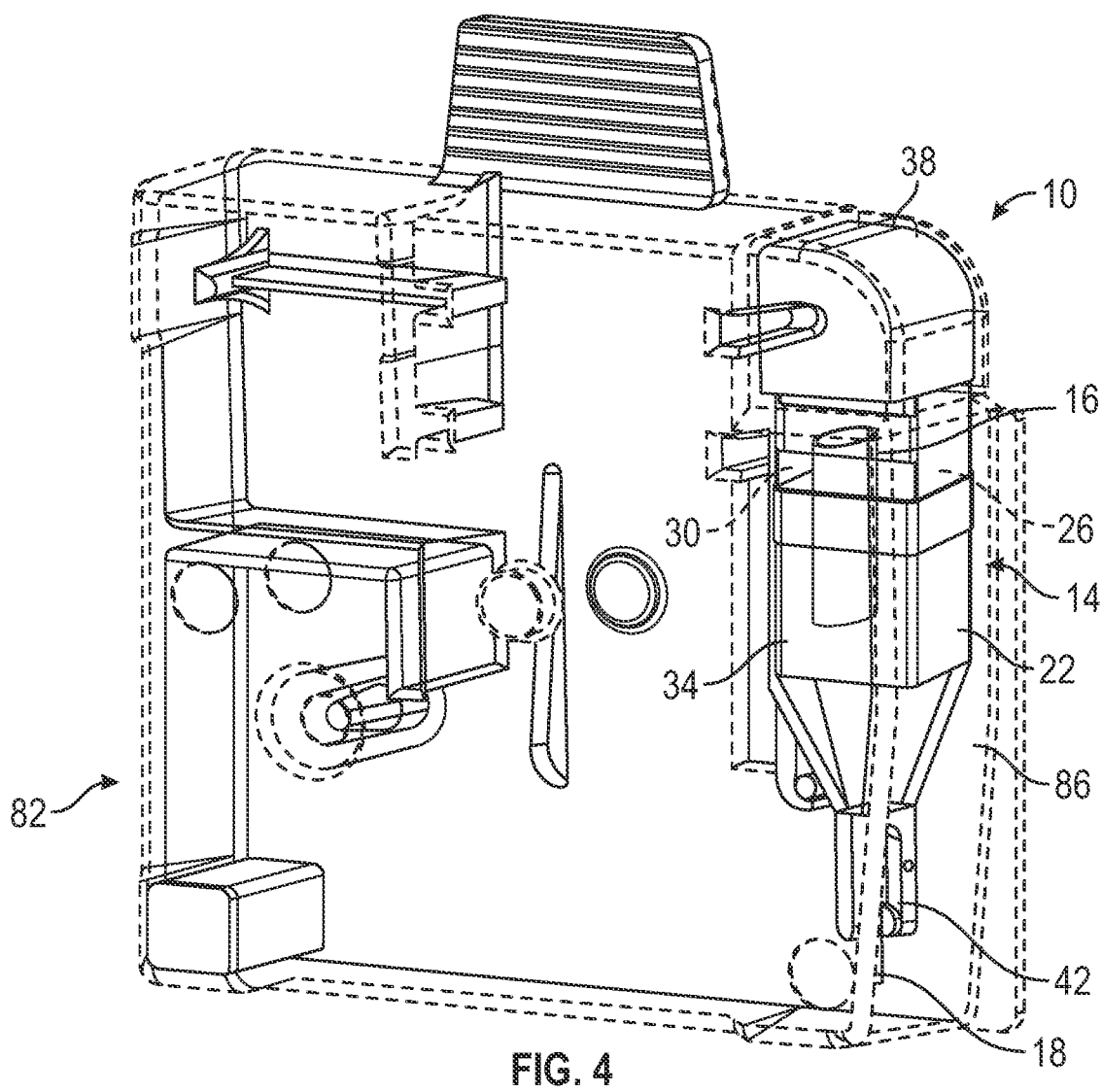
FIG. 4 is a perspective view of the liquid test sample dispensing device of FIG. 1 in which the at least one inner surface of the capillary is uniformly coated with at least one anticoagulant compound in accordance with presently disclosed and/or claimed inventive concept(s) and the liquid test sample dispensing device has been inserted into a reaction vessel for the conductance of at least one diagnostic assay.

Referring now to FIG. 4, shown therein is a perspective view of the liquid test sample dispensing device 10 of FIG. 1 in which at least one inner surface 50 of the capillary 18 is uniformly coated with an anticoagulant compound coating 78 and the liquid test sample dispensing device 10 has been inserted into a reaction vessel 82 for the conductance of at least one diagnostic assay. Following the collection of a patient's liquid test sample into the capillary 18 of the liquid test sample dispensing device 10, the liquid test sample dispensing device 10 is inserted into and secured within a reaction chamber 86 of a reaction vessel 82. In one non-limiting embodiment, the reaction vessel is then secured within a diagnostic assay system/instrument (such as, by way of example only, the DCA Vantage® Analyzer commercially available from Siemens Healthcare Diagnostics, Inc.). Once secured within the diagnostic assay system/instrument, the patient's liquid test sample is then dispensed from the capillary 18 into the reaction chamber 86 of the reaction vessel 82 via, for example, the automated rotation and agitation of the reaction vessel 82 within the diagnostic assay system/instrument. Following the dispensing of the patient's liquid test sample into the reaction chamber 86 of the reaction vessel 82, at least one diagnostic assay (such as, by way of example only, a glycated hemoglobin diagnostic assay) is conducted on the patient's liquid test sample. In one non-limiting embodiment, the at least one diagnostic assay involves pre-determined steps in which the reaction vessel 82 is rotated in both clockwise and counter clockwise directions such that the patient's liquid test sample is sufficiently mixed with both solid and liquid reagents, while various measurements are taken at pre-determined intervals during the conductance of the at least one diagnostic assay. At the conclusion of the at least one diagnostic assay, a volume of liquid waste is contained within the reaction vessel 82, the volume of liquid waste primarily comprising a mixture of the patient's liquid test sample, the solid reagent(s), and/or the liquid reagent(s) utilized in the conductance of the at least one diagnostic assay. Subsequent to the conclusion of the at least one diagnostic assay, the reaction vessel 82 containing the volume of liquid waste is substantially inverted via, for example, rotation of the reaction vessel 82 within the diagnostic assay system/instrument. This inversion allows the volume of liquid waste to come into contact with, when present, the liquid waste collector 16, such that the volume of liquid waste is absorbed by and contained/maintained within the liquid waste collector 16.

While shown throughout the majority of the Figures as being connected to a liquid test sample dispensing device when the at least one anticoagulant is placed on at least one inner surface of the capillary, it should be readily understood to a person having ordinary skill in the art that the capillaries may be separate from the liquid test sample dispensing device(s) when the at least one anticoagulant is applied to the at least one inner surface of each of the capillaries. In such instances, the capillaries can later be connected to the liquid test sample dispensing devices(s) or can be used for additional applications in accordance with the presently disclosed and/or claimed inventive concept(s).

Referring now to FIGS. 5A-5H, shown therein are perspective views of an alternative embodiment of a method for applying at least one anticoagulant compound on at least one inner surface of a plurality of capillaries in accordance with the presently disclosed and/or claimed inventive concept(s). While FIGS. 5A-5H depict four separate capillaries, it should be readily understood to a person having ordinary skill in the art that the presently disclosed and/or claimed methodology can include any number of capillaries, for instance, by way of example only, 1, 2, 3, 4, 5, 6, 7, 8, 9, 10, 11, 12, 13, 14, 15, 16, 17, 18, 19, 20, 25, 30, 35, 40, 45, 50, 55, 60, 70, 75, 80, 85, 90, 95, or greater than or equal to 100 capillaries. The capillaries may be attached to one another via a mechanical connecting web 210. In addition, the process of sequentially disposing the first capillary 218A, the second capillary 218B, the third capillary 218C, and the fourth capillary 218D within a receptacle 258 containing a colloidal solution 262 comprising at least one anticoagulant compound (for instance, by way of example only, heparin) and at least one insoluble volatile compound (for instance, by way of example only, acetone) can be accomplished either by a manual or automated process(es) via use of the mechanical web 210. While shown in FIGS. 5A-5H as being identical in configuration, the first capillary 218A, second capillary 218B, the third capillary 218C, and the fourth capillary 218D need not be the same configuration and can be of any size and/or shape that accomplishes the presently disclosed and/or claimed inventive concept(s).

Figure 5A:
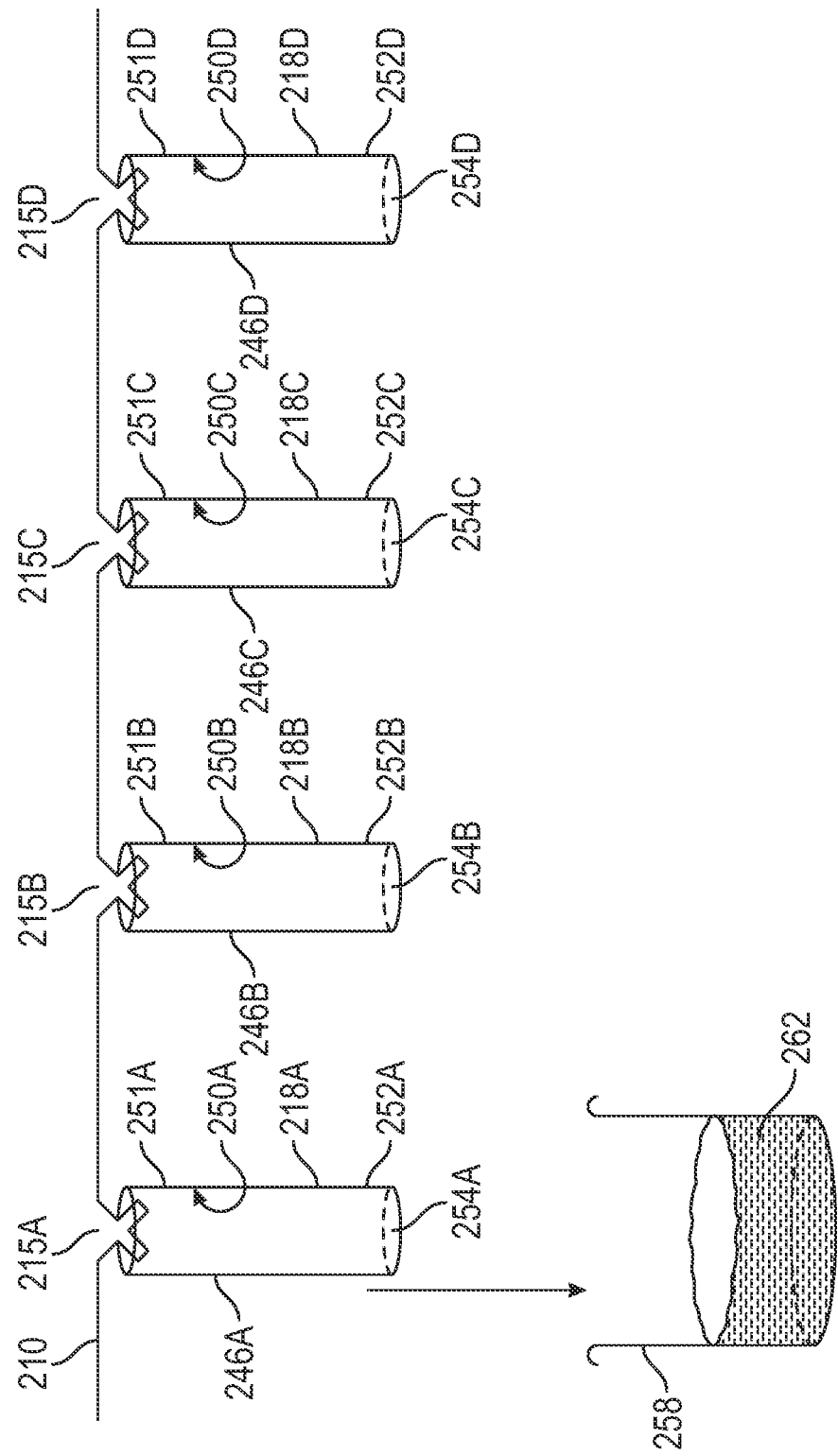
Figure 5B:
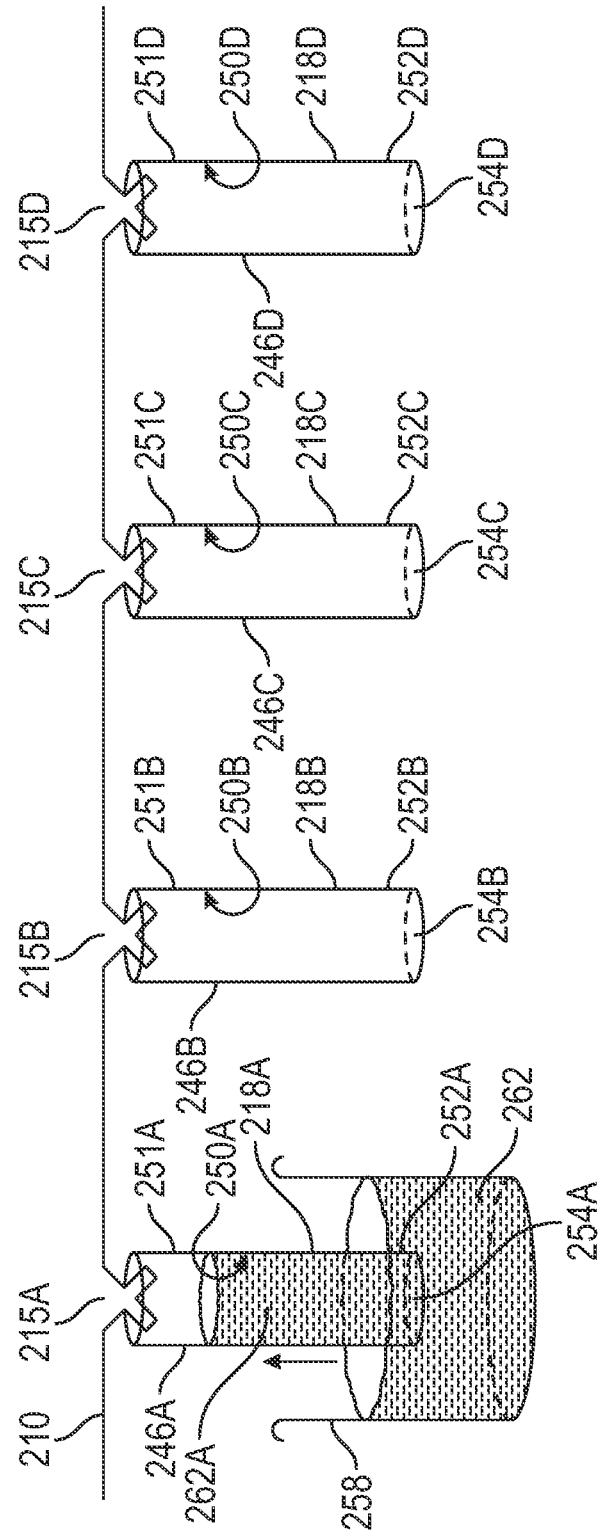

As shown in FIGS. 5A-5B, the first capillary 218A is connected to the mechanical web 210 via a first capillary holder 215A. The first capillary 218A comprises at least one outer surface 246A, at least one inner surface 250A, a first end 251A, a second end 252A, and an opening 254A located at the second end 252A for receiving the colloidal solution 262 via, by way of example only, capillary action. As shown in FIGS. 5A-5B, the first capillary 218A is lowered from the mechanical web 215 into the receptacle 258 such that the opening 254A is submerged within the colloidal solution 262. As a result of this submersion, the colloidal solution 262 wicks through the opening 254A (for instance, via capillary action) such that the colloidal solution 262 is in fluid contact with at least a portion of the at least one inner surface 250A and remains (as a result of capillary force) within the first capillary 218A for further processing in accordance with the presently disclosed and/or claimed inventive concept(s). After the colloidal solution 262 is wicked through the opening 254A of the first capillary 218A, the second capillary 218B is transitioned so that it is capable of being disposed within the receptacle 258.

Figure 5C:
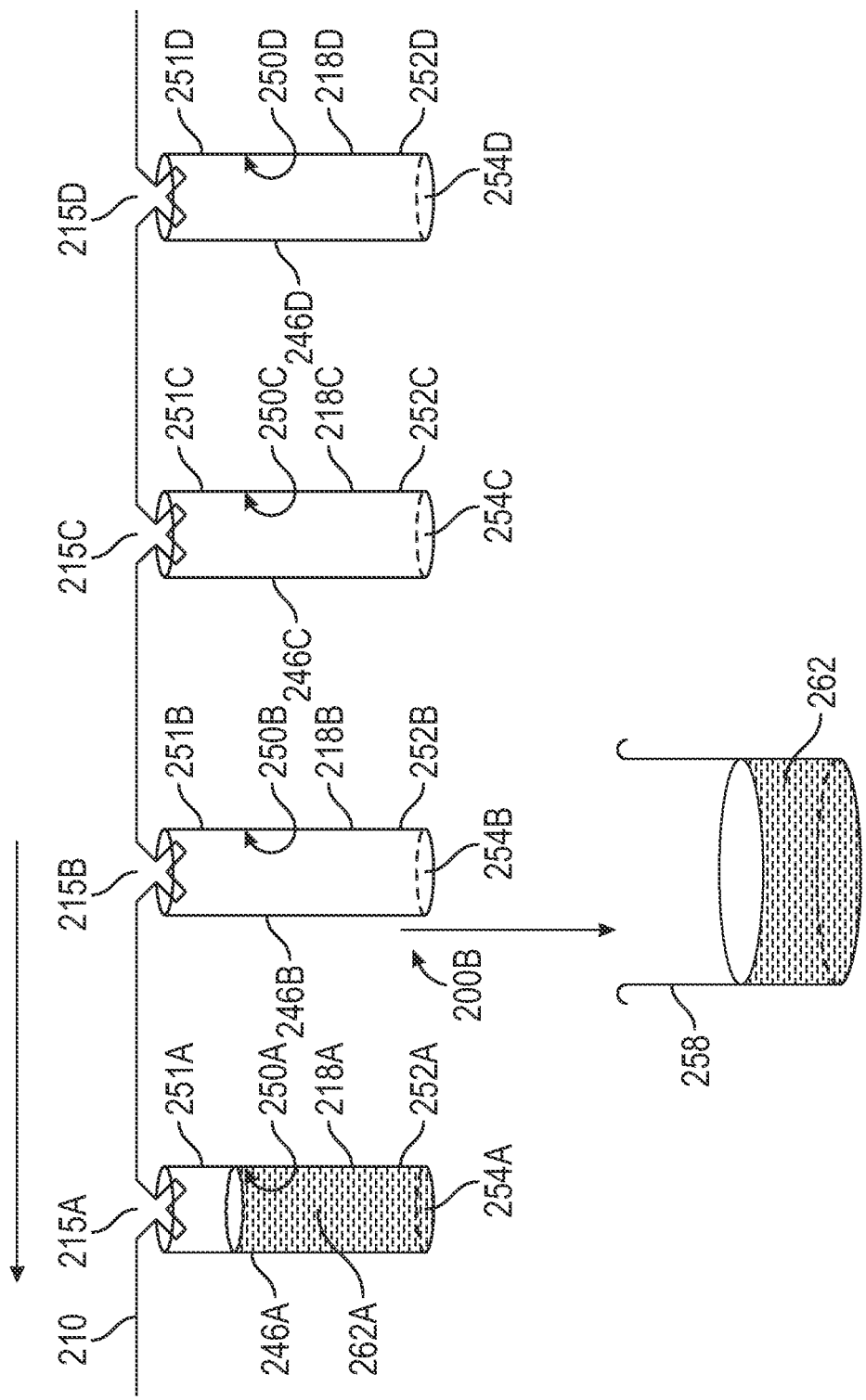
Figure 5D:
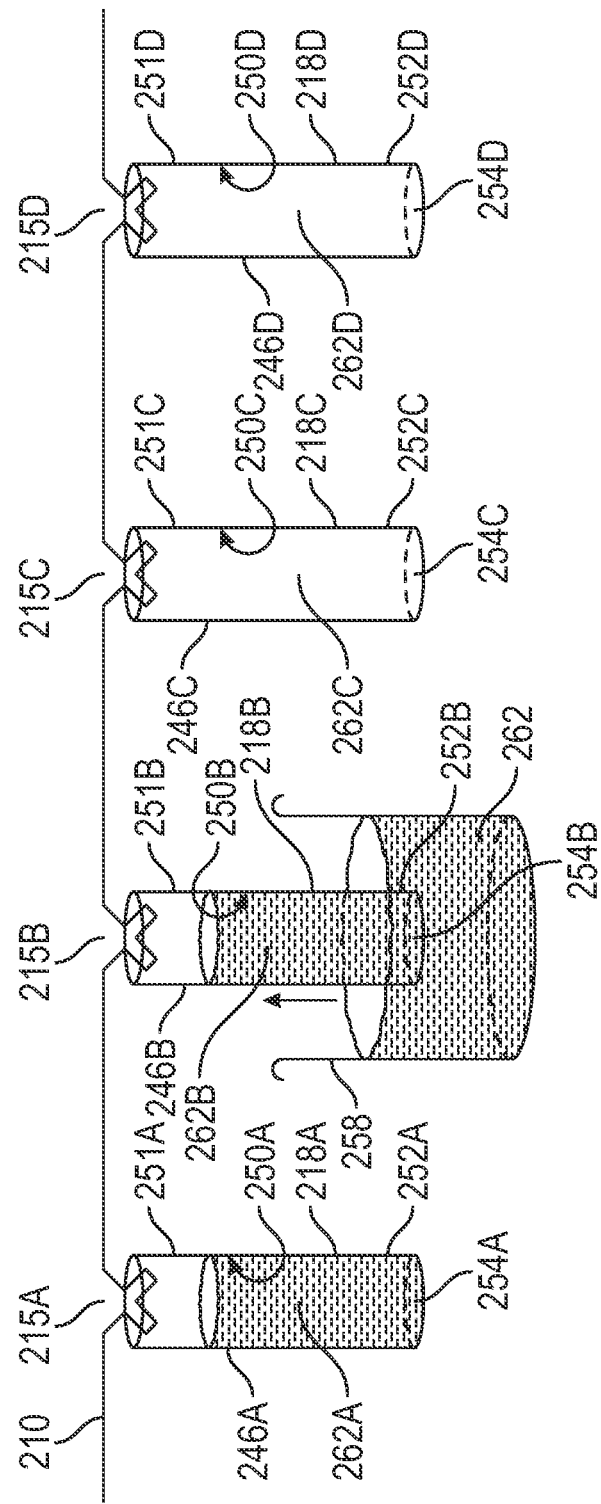

Referring now to FIGS. 5C-5D, the second capillary 218B is connected to the mechanical web 210 via a second capillary holder 215B. The second capillary 218B comprises at least outer surface 246B, at least one inner surface 250B, a first end 251B, a second end 252B, and an opening 254B located at the second end 252B for receiving the colloidal solution 262 via, by way of example only, capillary action. As shown in FIGS. 5C-5D, the second capillary 218B is lowered from the mechanical web 215 into the receptacle 258 such that the opening 254B is submerged within the colloidal solution 262. As a result of this submersion, the colloidal solution 262 wicks through the opening 254B (for instance, via capillary action) such that the colloidal solution 262 is in fluid contact with at least a portion of the at least one inner surface 250B and remains (as a result of capillary force) within the second capillary 218B for further processing in accordance with the presently disclosed and/or claimed inventive concept(s). After the colloidal solution 262 is wicked through the opening 254B of the second capillary 218B, the third capillary 218C is transitioned so that it is capable of being disposed within the receptacle 258.

Figure 5E:
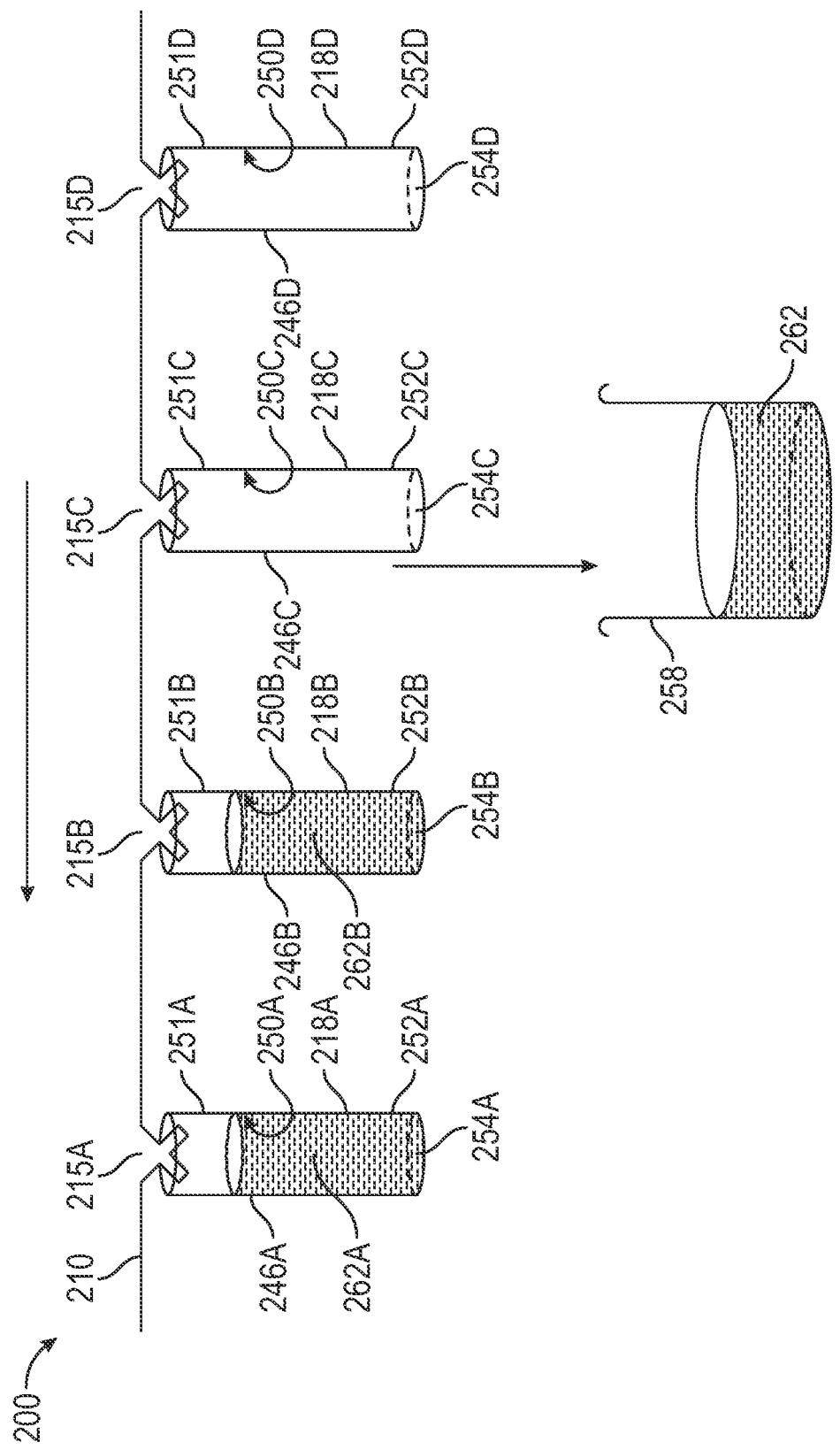
Figure 5F:
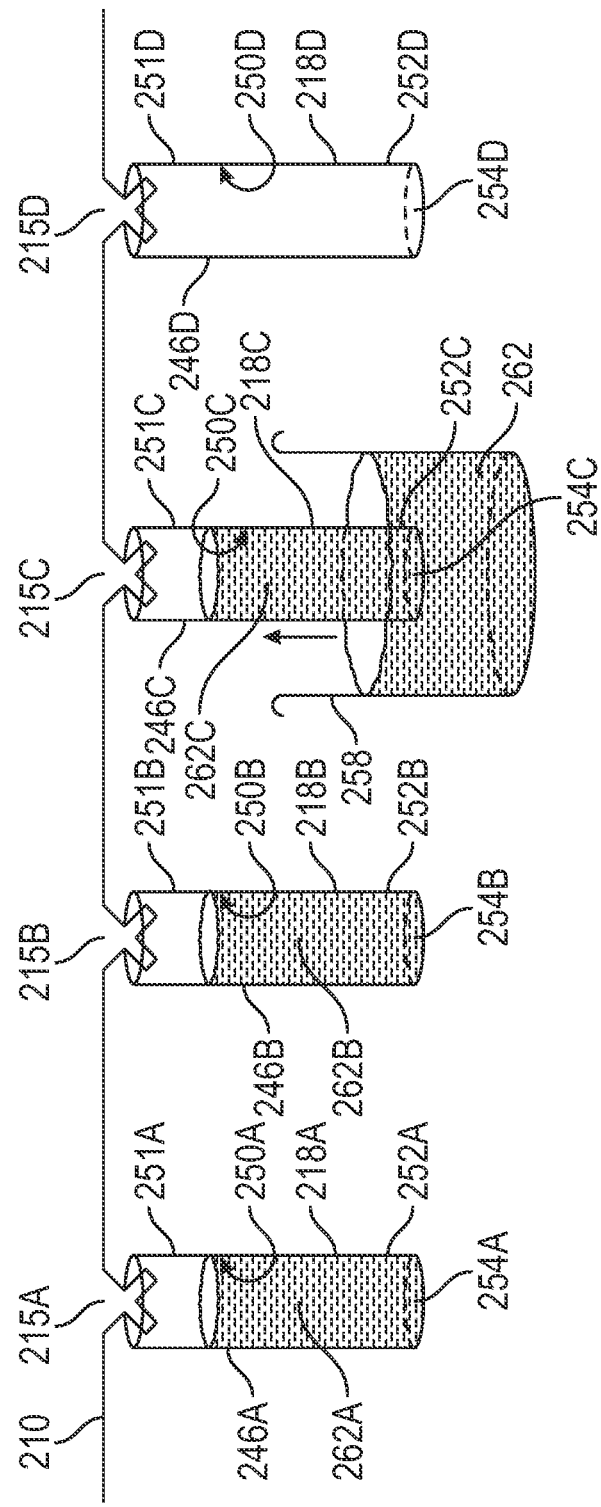

Referring now to FIGS. 5E-5F, the third capillary 218C is connected to the mechanical web 210 via a third capillary holder 215C. The third capillary 218C comprises at least outer surface 246C, at least one inner surface 250C, a first end 251C, a second end 252C, and an opening 254C located at the second end 252C for receiving the colloidal solution 262 via, by way of example only, capillary action. As shown in FIGS. 5E-5F, the third capillary 218C is lowered from the mechanical web 215 into the receptacle 258 such that the opening 254C is submerged within the colloidal solution 262. As a result of this submersion, the colloidal solution 262 wicks through the opening 254C (for instance, via capillary action) such that the colloidal solution 262 is in fluid contact with at least a portion of the at least one inner surface 250C and remains (as a result of capillary force) within the third capillary 218C for further processing in accordance with the presently disclosed and/or claimed inventive concept(s). After the colloidal solution 262 is wicked through the opening 254C of the third capillary 218B, the fourth capillary 218D is transitioned so that it is capable of being disposed within the receptacle 258.

Figure 5G:
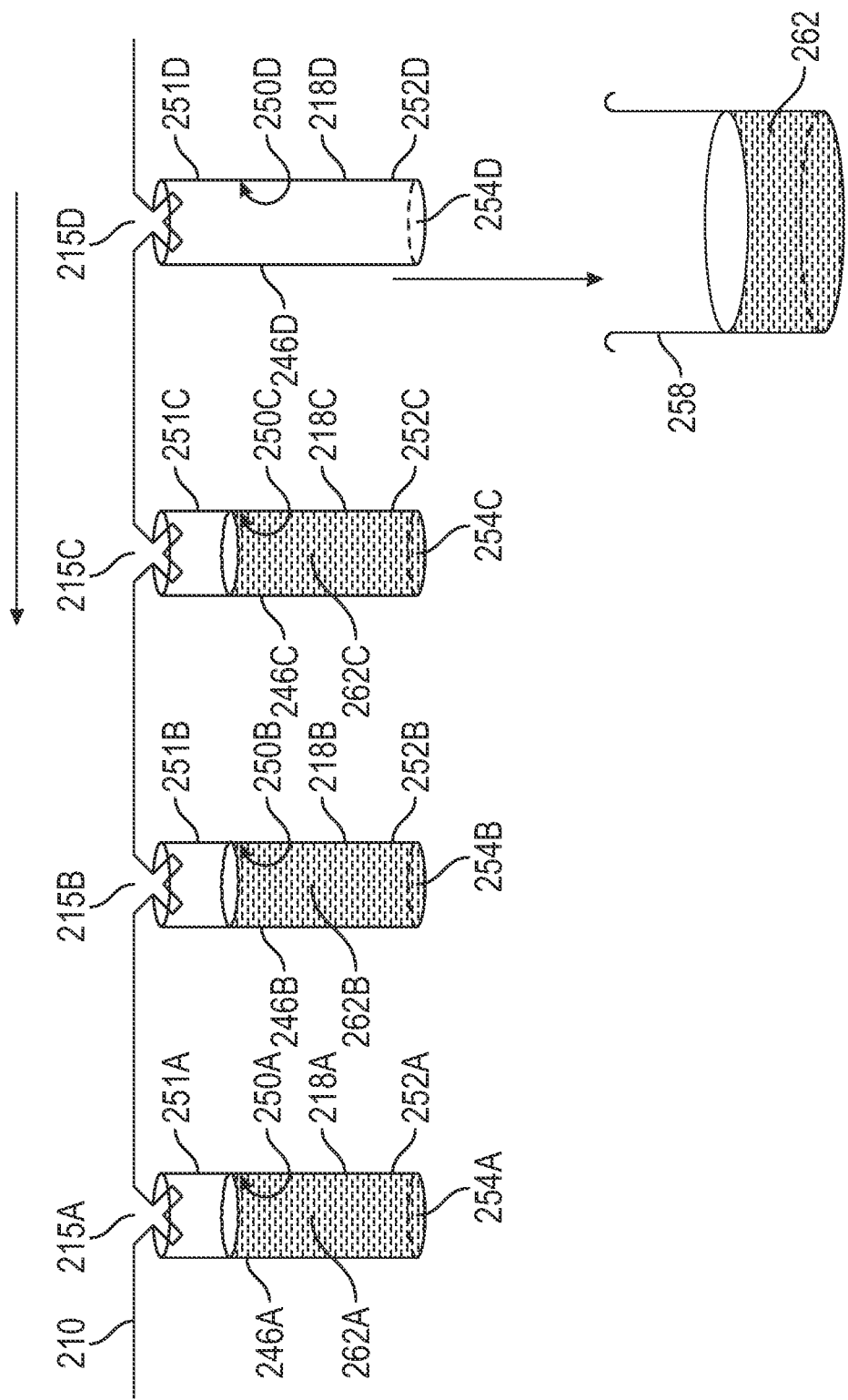

Referring now to FIGS. 5G-5H, the fourth capillary 218D is connected to the mechanical web 210 via a fourth capillary holder 215D. The fourth capillary 218D comprises at least outer surface 246D, at least one inner surface 250D, a first end 251D, a second end 252D, and an opening 254D located at the second end 252D for receiving the colloidal solution 262 via, by way of example only, capillary action. As shown in FIGS. 5G-5H, the fourth capillary 218D is lowered from the mechanical web 215 into the receptacle 258 such that the opening 254D is submerged within the colloidal solution 262. As a result of this submersion, the colloidal solution 262 wicks through the opening 254B (for instance, via capillary action) such that the colloidal solution 262 is in fluid contact with at least a portion of the at least one inner surface 250D and remains (as a result of capillary force) within the fourth capillary 218D for further processing in accordance with the presently disclosed and/or claimed inventive concept(s).

The above process is repeated for each capillary attached to the mechanical web 210 such that each capillary contains the colloidal solution 262.

With respect to FIGS. 5A-5H, the colloidal solution 262 is maintained in the receptacle 258 at a temperature that is below the evaporation temperature of the at least one insoluble volatile compound of the colloidal solution 262. In one non-limiting embodiment, the at least one insoluble volatile compound is acetone and the temperature of the colloidal solution 262 is maintained in the receptacle 258 in a range from about 0° C. to about 55° C., or from about 5° C. to about 50° C., or from about 10° C. to about 45° C., or from about 15° C. to about 40° C., or from about 20° C. to about 35° C., or from about 25° C. to about 30° C. In one non-limiting embodiment, the colloidal solution 262 is maintained at a temperature of about 25° C.

Once the colloidal solution 262 has been wicked into and is contained within the first capillary 218A, the second capillary 218B, the third capillary 218C, and the fourth capillary 218D (and any other capillaries that may be attached to the mechanical web 210), the first capillary 218A, the second capillary 218B, the third capillary 218C, and the fourth capillary 218D (and any other capillaries that may be attached to the mechanical web 201) are heated to evaporate off and remove the at least one insoluble volatile compound contained within the colloidal solution 262. The heating can be accomplished via: (1) either by transitioning the mechanical web 210 through a heater such that all of the capillaries are simultaneously heated; and/or (2) by removing the capillaries from the mechanical web and placing them either individually or collectively into a heater. However, at all times, the agitation of the capillaries must be mitigated to ensure that colloidal solution 262 remains contained within the capillaries. At this stage, the heating is conducted at a temperature that is high enough to evaporate the insoluble volatile compound(s) (for instance, acetone), but low enough so as not to melt the anticoagulant compound(s) (for instance, heparin granules, which are deposited on the at least one inner surfaces 250A, 250B, 250C, and 250D of each of the capillaries 218A, 218B, 218C, and 218D, respectively), as the insoluble volatile compound(s) evaporates). In one non-limiting embodiment, the at least one insoluble volatile compound is acetone and the colloidal solution 262 contained within the capillaries 218A, 218B, 218C, and 218D is heated to and maintained at a temperature from about 55° C. to about 125° C., or from about 60° C. to about 120° C., or from about 65° C. to about 115° C., or from about 70° C. to about 110° C., or from about 75° C. to about 105° C., or from about 80° C. to about 100° C., or from about 85° C. to about 95° C., or from about greater than or equal to 90° C. In one non-limiting embodiment, the capillaries 218A-218D are heated to a temperature of about 100° C. to evaporate off and remove the at least one insoluble volatile compound from the colloidal solution 262 contained within the capillaries 218A-218D. The capillaries 218A-218D can be heated via any method commonly known in the art provided that the colloidal solution 262 remains in contact with each of the at least one inner surfaces 250A-250D of the capillaries 218A-218D prior to and during the evaporation of the at least one insoluble volatile compound(s), including, without limitation, via commercial-grade dryers and/or vacuum dryers commonly known in the art.

Following the evaporation of the at least one insoluble volatile compound from the at least one inner surfaces 250A-250D of the capillaries 218A-218D, non-uniform anticoagulant compound granules (for instance, heparin granules) are deposited on the at least one inner surfaces 250A-250D of the capillaries 218A-218D. The anticoagulant compound granules, due to their potential to form non-uniform shape(s), may form granular plugs within the capillaries 218A-218D that inhibit or eliminate the ability of the capillaries 218A-218D to effectively draw in a patient's liquid test sample. If present, the non-uniform anticoagulant compound granules may be heated such that the anticoagulant compound granules are melted to form a uniform, even coat which substantially covers the entirety of each of the at least one inner surfaces 250A-250D of the capillaries 218A-218D without restricting the openings 254A-254D or the bores (not numbered) of the capillaries 218A-218D from being able to wick in a patient's liquid test sample via capillary action. When the anticoagulant compound granules are heparin granules, the capillaries 218A-218D may be heated to a temperature of from about 130° C. to about 200° C., or from about 135° C. to about 195° C., or from about 140° C. to about 190° C., or from about 145° C. to about 185° C., or from about 150° C. to about 180° C., or from about 155° C. to about 175° C., or from about 160° C. to about 170° C., or greater than or equal to about 165° C. to allow the heparin granules to sufficiently melt to form a uniform heparin coating on each of the at least one inner surfaces 250A-250D of the capillaries 218A-218D. The capillaries 218A-218D may be heated via any method commonly known in the art, including, without limitation, via commercial-grade dryers.

At this stage, the capillaries 218A-218D are ready to be attached to their respective liquid test sample dispensing devices for the collection of a patient's liquid test sample for the conductance of at least one diagnostic assay or to be used for additional applications contemplated by the presently disclosed and/or claimed inventive concept(s).

Non-limiting Examples of the Inventive Concept(s)

A method for coating an internal surface of a capillary of a liquid test sample dispensing device with at least one anticoagulant compound, the method comprising the steps of: (a) preparing a colloidal solution, the colloidal solution comprising at least one anticoagulant compound and at least one insoluble volatile compound, the colloidal solution being contained within a receptacle; (b) placing a liquid test sample dispensing device into the receptacle, the liquid test sample dispensing device comprising: a body, the body comprising at least one side, a first end, and a second end; and a capillary portion, the capillary portion comprising a capillary having at least one outer surface, at least one inner surface, a first end, a second end, and an opening located at the second end of the capillary, wherein the first end of the capillary is disposed through the second end of the body, and further wherein the capillary is in fluid contact with the colloidal solution such that a volume of the colloidal solution enters into and is retained within the capillary via the opening such that the colloidal solution is in fluid contact with the at least one inner surface of the capillary; and (c) removing the liquid test sample dispensing device from the receptacle and heating at least the capillary portion of the liquid test sample dispensing device to a temperature wherein the at least one insoluble volatile compound evaporates from the colloidal solution contained within the capillary, further wherein granules of the at least one anticoagulant compound are deposited on the at least one inner surface of the capillary.

The method, wherein the at least one anticoagulant compound is selected from the group consisting of acenocoumarol, dicoumarol, ethyl bicoumacetate, atromentin, phenindione, phenprocoumon, tecafarin, and warfarin acenocoumarol, dicoumarol, ethyl bicoumacetate, atromentin, phenindione, phenprocoumon, tecafarin, and warfarin, coumarin, heparin and heparin derivatives, fondaparinux, idraparinux, rivaroxaban, apixaban, edoxaban, betrixaban, darexaban, letaxaban, and eribaxaban, hirudin, lepirudin, bivalirudin, argatroban, dabigatran, batraxobin, hementin, vitamin E, ethylenediaminetetraacetic acid (EDTA), citrate, oxalate, and combinations thereof.

The method, wherein the at least one insoluble volatile compound is selected from the group consisting of acetone, benzene, ethyl acetate, hexane, methyl acetate, toluene, and combinations thereof.

The method, wherein the capillary portion in step (c) is heated to a temperature ranging from about 55° C. to about 150° C.

The method, wherein the capillary portion is heated via a heater selected from the group consisting of a commercial-grade dryer, a vacuum dryer, and combinations thereof.

The method, further comprising the step: (d) heating the granules of the at least one anticoagulant compound to a temperature that melts the granules and thereby forms a uniform coating of the at least one anticoagulant compound on the at least one inner surface of the capillary.

The method, wherein the granules of the at least one anticoagulant compound is heated to a temperature ranging from about 170° C. to about 200° C.

A method for conducting at least one diagnostic assay of a patient's liquid test sample, the method comprising the steps of: (a) preparing a colloidal solution, the colloidal solution comprising at least one anticoagulant compound and at least one insoluble volatile compound, the colloidal solution being contained within a receptacle; (b) placing a liquid test sample dispensing device into the receptacle, the liquid test sample dispensing device comprising: a body, the body comprising at least one side, a first end, and a second end; and a capillary portion, the capillary portion comprising a capillary having at least one outer surface, at least one inner surface, a first end, a second end, and an opening located at the second end of the capillary, wherein the first end of the capillary is disposed through the second end of the body, further wherein the capillary is in fluid contact with the colloidal solution such that a volume of the colloidal solution enters into and is retained within the capillary via the opening such that the colloidal solution is in fluid contact with the at least one inner surface of the capillary; (c) removing the liquid test sample dispensing device from the receptacle and heating at least the capillary portion of the liquid test sample dispensing device to a temperature wherein the at least one insoluble volatile compound evaporates from the colloidal solution contained within the capillary, and further wherein granules of the at least one anticoagulant compound are deposited on the at least one inner surface of the capillary; (d) collecting a patient's liquid test sample within the capillary comprising the granules of the at least one anticoagulant compound of the liquid test sample dispensing device; (e) inserting the liquid test sample dispensing device containing the patient's collected liquid test sample into a reaction vessel for conductance of at least one diagnostic assay of the patient's collected liquid test sample; and (f) conducting the at least one diagnostic assay.

The method, wherein the patient's liquid test sample is whole blood.

The method, wherein the at least one diagnostic assay is a glycated hemoglobin diagnostic assay.

The method, wherein the at least one anticoagulant compound is selected from the group consisting of acenocoumarol, dicoumarol, ethyl bicoumacetate, atromentin, phenindione, phenprocoumon, tecafarin, and warfarin acenocoumarol, dicoumarol, ethyl bicoumacetate, atromentin, phenindione, phenprocoumon, tecafarin, and warfarin, coumarin, heparin and heparin derivatives, fondaparinux, idraparinux, rivaroxaban, apixaban, edoxaban, betrixaban, darexaban, letaxaban, and eribaxaban, hirudin, lepirudin, bivalirudin, argatroban, dabigatran, batraxobin, hementin, vitamin E, ethylenediaminetetraacetic acid (EDTA), citrate, oxalate, and combinations thereof.

The method, wherein the at least one insoluble volatile compound is selected from the group consisting of acetone, benzene, ethyl acetate, hexane, methyl acetate, toluene, and combinations thereof.

The method, wherein the capillary portion in step (c) is heated to a temperature ranging from about 55° C. to about 150° C.

The method, wherein the capillary portion is heated via a heater selected from the group consisting of a commercial-grade dryer, a vacuum dryer, and combinations thereof.

The method, further comprising the step of heating the granules of the at least one anticoagulant compound to a temperature that melts the granules and thereby forms a uniform coating of the at least one anticoagulant compound on the at least one inner surface of the capillary prior to the collection of the patient's liquid test sample.

The method, wherein the granules of the at least one anticoagulant compound is heated to a temperature ranging from about 170° C. to about 200° C.

Thus, in accordance with the presently disclosed and claimed inventive concept(s), there have been provided methods, devices, and kits for uniformly coating at least one inner surface of a capillary of a liquid test sample dispensing device with at least one anticoagulant compound. As described herein, the presently disclosed and claimed inventive concept(s) relate both increase the amount a time a patient's liquid test sample can be contained within the capillary (i.e., before the patient's liquid test sample coagulates) and for the full-dispensing of the patient's liquid test sample into a reaction vessel for the conductance of at least one diagnostic assay. Such presently disclosed and/or claimed inventive concept(s) fully satisfy the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A method of using a liquid test sample dispensing device to dispense a patient's liquid test sample into a reaction vessel for conductance of at least one diagnostic assay, the method comprising the steps of:
   (a) preparing a colloidal solution, the colloidal solution comprising at least one anticoagulant compound and at least one insoluble volatile compound, the colloidal solution being contained within a receptacle;
   (b) placing a liquid test sample dispensing device into the receptacle, the liquid test sample dispensing device comprising:
      a body, the body comprising at least one side, a first end, and a second end; and
      a capillary portion, the capillary portion comprising a capillary having at least one outer surface, at least one inner surface, a first end, a second end, and an opening located at the second end of the capillary, wherein the first end of the capillary is disposed through the second end of the body, further wherein the capillary is in fluid contact with the colloidal solution such that a volume of the colloidal solution enters into and is retained within the capillary via the opening such that the colloidal solution is in fluid contact with the at least one inner surface of the capillary;
   (c) removing the liquid test sample dispensing device from the receptacle and heating at least the capillary portion of the liquid test sample dispensing device to a temperature wherein the at least one insoluble volatile compound evaporates from the colloidal solution contained within the capillary, and further wherein granules of the at least one anticoagulant compound are deposited on the at least one inner surface of the capillary;
   (d) drawing the patient's liquid test sample into the capillary of the liquid test sample dispensing device, wherein the capillary has the at least one anticoagulant compound's granules deposited on the at least one inner surface of thereof; and
   (e) inserting the liquid test sample dispensing device containing the patient's collected liquid test sample into the reaction vessel for conductance of at least one diagnostic assay of the patient's collected liquid test sample.

2. The method of claim 1, wherein the patient's liquid test sample is whole blood.

3. The method of claim 1, wherein the at least one anticoagulant compound is selected from the group consisting of acenocoumarol, dicoumarol, ethyl bicoumacetate, atromentin, phenindione, phenprocoumon, tecafarin, and warfarin acenocoumarol, dicoumarol, ethyl bicoumacetate, atromentin, phenindione, phenprocoumon, tecafarin, and warfarin, coumarin, heparin and heparin derivatives, fondaparinux, idraparinux, rivaroxaban, apixaban, edoxaban, betrixaban, darexaban, letaxaban, and eribaxaban, hirudin, lepirudin, bivalirudin, argatroban, dabigatran, batraxobin, hementin, vitamin E, ethylenediaminetetraacetic acid (EDTA), citrate, oxalate, and combinations thereof.

4. The method of claim 1, wherein the at least one insoluble volatile compound is selected from the group consisting of acetone, benzene, ethyl acetate, hexane, methyl acetate, toluene, and combinations thereof.

5. The method of claim 1, wherein the capillary portion in step (c) is heated to a temperature ranging from about 55° C. to about 150° C.

6. The method of claim 5, wherein the capillary portion is heated via a heater selected from the group consisting of a commercial-grade dryer, a vacuum dryer, and combinations thereof.

7. The method of claim 1, further comprising the step of heating the granules of the at least one anticoagulant compound to a temperature that melts the granules and thereby forms a uniform coating of the at least one anticoagulant compound on the at least one inner surface of the capillary prior to the collection of the patient's liquid test sample.

8. The method of claim 7, wherein the granules of the at least one anticoagulant compound is heated to a temperature ranging from about 170° C. to about 200° C.

* * * * *